(12) United States Patent
Moffitt et al.

(10) Patent No.: US 9,216,282 B1
(45) Date of Patent: Dec. 22, 2015

(54) ELECTRODE CONFIGURATIONS FOR ELECTRICAL STIMULATION SYSTEMS AND METHODS OF MAKING AND USING

(75) Inventors: Michael Adam Moffitt, Valencia, CA (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1670 days.

(21) Appl. No.: 11/855,033

(22) Filed: Sep. 13, 2007

(51) Int. Cl.
*A61N 1/05* (2006.01)

(52) U.S. Cl.
CPC .................................. *A61N 1/0553* (2013.01)

(58) Field of Classification Search
USPC .......................................... 607/115–129, 132
See application file for complete search history.

(56) References Cited

U.S. PATENT DOCUMENTS

| | | | |
|---|---|---|---|
| 3,718,142 | A | 2/1973 | Mulier |
| 5,193,539 | A | 3/1993 | Schulman et al. |
| 5,193,540 | A | 3/1993 | Schulman et al. |
| 5,312,439 | A | 5/1994 | Loeb et al. |
| 5,417,719 | A | 5/1995 | Hull et al. |
| 5,902,236 | A * | 5/1999 | Iversen ..................... 623/23.65 |
| 6,038,484 | A | 3/2000 | Kuzma |
| 6,051,017 | A | 4/2000 | Loeb et al. |
| 6,181,969 | B1 | 1/2001 | Gord |
| 6,185,463 | B1 | 2/2001 | Baudino |
| 6,343,226 | B1 | 1/2002 | Sunde et al. |
| 6,473,653 | B1 * | 10/2002 | Schallhorn et al. ........... 607/116 |
| 6,516,227 | B1 | 2/2003 | Meadows et al. |
| 6,604,283 | B1 | 8/2003 | Kuzma |
| 6,609,029 | B1 | 8/2003 | Mann et al. |
| 6,609,032 | B1 | 8/2003 | Woods et al. |
| 6,741,892 | B1 | 5/2004 | Meadows et al. |
| 6,757,970 | B1 | 7/2004 | Kuzma et al. |
| 6,999,820 | B2 | 2/2006 | Jordan |
| 7,107,104 | B2 | 9/2006 | Keravel et al. |
| 2002/0022873 | A1 * | 2/2002 | Erickson et al. .............. 607/117 |
| 2002/0062143 | A1 | 5/2002 | Baudino et al. |
| 2004/0059392 | A1 | 3/2004 | Parramon et al. |
| 2004/0260310 | A1 | 12/2004 | Harris |
| 2005/0246004 | A1 | 11/2005 | Cameron et al. |
| 2006/0253182 | A1 | 11/2006 | King |
| 2007/0060991 | A1 | 3/2007 | North et al. |

(Continued)

FOREIGN PATENT DOCUMENTS

| | | |
|---|---|---|
| WO | 98/37926 | 9/1998 |
| WO | 98/43700 | 10/1998 |

(Continued)

OTHER PUBLICATIONS

U.S. Appl. No. 11/238,240, filed Sep. 29, 2005 (19 pages).

(Continued)

*Primary Examiner* — Erica Lee
(74) *Attorney, Agent, or Firm* — Lowe Graham Jones PLLC; Bruce E. Black

(57) ABSTRACT

A paddle lead can include a plurality of first electrodes disposed entirely on a first major surface of the lead body and a plurality of second electrodes disposed entirely on a second major surface of the lead body. A paddle lead may include a plurality of electrodes in at least one column on a paddle body and a strip electrode disposed on the paddle body. A lead may include a lead body with an ellipse-like cross-section and a plurality of electrodes disposed circumferentially around the lead body and proximate to a distal end of the lead body.

12 Claims, 4 Drawing Sheets

(56) References Cited

U.S. PATENT DOCUMENTS

| | | |
|---|---|---|
| 2007/0073356 A1* | 3/2007 | Rooney et al. .................. 607/46 |
| 2007/0150007 A1 | 6/2007 | Anderson et al. |
| 2007/0150034 A1 | 6/2007 | Rooney et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0179579 A1 | 8/2007 | Feler et al. |
| 2007/0219595 A1 | 9/2007 | He |
| 2007/0239243 A1 | 10/2007 | Moffitt et al. |
| 2007/0255372 A1 | 11/2007 | Metzler et al. |
| 2008/0004674 A1* | 1/2008 | King et al. ...................... 607/46 |
| 2008/0004675 A1 | 1/2008 | King et al. |

FOREIGN PATENT DOCUMENTS

| | | |
|---|---|---|
| WO | 98/43701 | 10/1998 |
| WO | 0117315 | 3/2001 |
| WO | 2007101999 A2 | 9/2007 |

OTHER PUBLICATIONS

U.S. Appl. No. 11/319,291, filed Dec. 27, 2005.
U.S. Appl. No. 11/327,880, filed Jan. 9, 2006.
U.S. Appl. No. 11/369,309, filed Mar. 6, 2006.
U.S. Appl. No. 11/375,638, filed Mar. 14, 2006.
U.S. Appl. No. 11/393,991, filed Mar. 30, 2006.

* cited by examiner

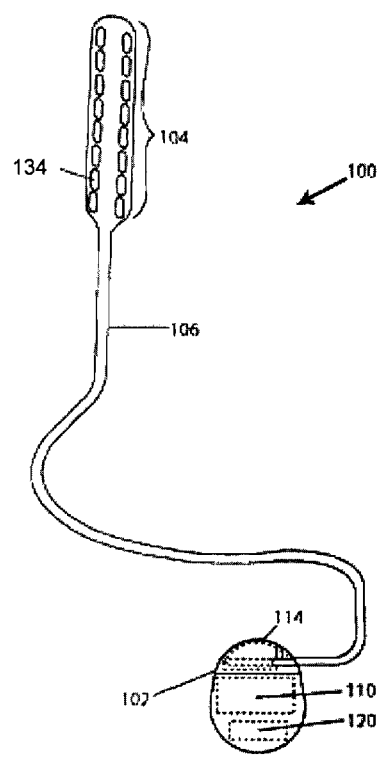
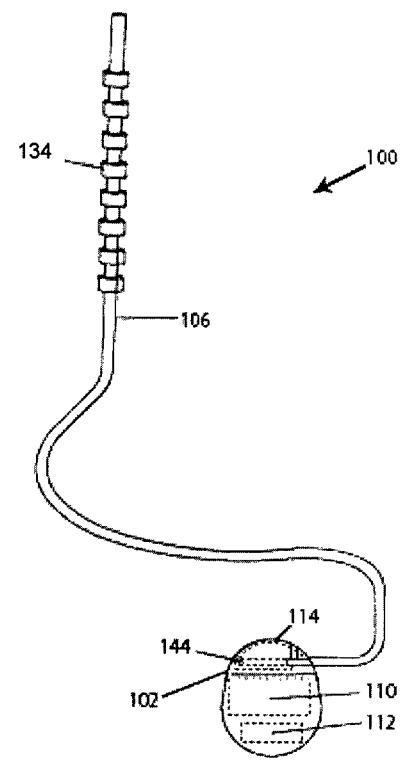
Fig. 1
Fig. 2

ELECTRODE CONFIGURATIONS FOR ELECTRICAL STIMULATION SYSTEMS AND METHODS OF MAKING AND USING

FIELD

The present invention is directed to the area of implantable electrical stimulation systems and methods of making and using the systems. The present invention is also directed to implantable electrical stimulation systems that include a percutaneous or paddle lead with an array of electrodes disposed on the lead, as well as methods of making and using the systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a paddle lead including a paddle body having a first major surface and a second major surface opposite the first major surface; a plurality of first electrodes disposed entirely on the first major surface; and a plurality of second electrodes disposed entirely on the second major surface.

Another embodiment is a paddle lead including a paddle body having a first major surface; a plurality of first electrodes disposed on the first major surface in at least one column; and a first strip electrode disposed on the paddle body.

Yet another embodiment is a lead including a lead body comprising at least a portion with an ellipse-like cross-section having a first major axis and a second major axis, wherein the first and second major axes have different lengths; and a plurality of first electrodes disposed circumferentially around the lead body and proximate to a distal end of the lead body.

Another embodiment is a lead including a paddle body having a longitudinal axis extending from a proximal end to a distal end of the paddle body; and a plurality of electrodes disposed in at least a first column, a second column, and a third column on the paddle body. The first column, second column, and third column are parallel to the longitudinal axis of the paddle body and each of the first, second, and third columns includes at least one of the plurality of electrodes. The first and second columns are adjacent and separated by a first lateral distance. The second and third columns are adjacent and separated by a second lateral distance. The first and second lateral distance are different.

Each of the leads can be used in a stimulation system where the lead is coupled to a control unit. Each of the leads can be used to stimulate tissue by disposing the lead near the tissue to be stimulated and providing an electrical signal to one or more of the electrodes of the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 1 is a schematic view of one embodiment of an electrical stimulation system, according to the invention;

FIG. 2 is a is a schematic view of another embodiment of an electrical stimulation system, according to the invention;

DETAILED DESCRIPTION

Figure 3:
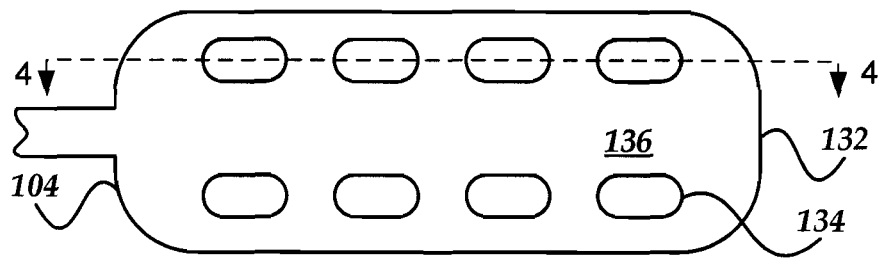
FIG. 3 is a schematic top view of one embodiment of a paddle body for use in an electrical stimulation system, according to the invention.

The present invention is directed to the area of implantable electrical stimulation systems and methods of making and using the systems. The present invention is also directed to implantable electrical stimulation systems that include a percutaneous or paddle lead with an array of electrodes disposed on the lead, as well as methods of making and using the systems.

Suitable implantable electrical stimulation systems include, but are not limited to, an electrode lead with one or more electrodes disposed on a distal end of the lead and one or more terminals disposed on a proximal end of the lead. Electrodes leads include, for example, percutaneous leads and paddle leads. Examples of stimulation systems with electrode leads are found in, for example, U.S. Pat. Nos. 6,181,969; 6,516,227; 6,609,029; 6,609,032; and 6,741,892; and U.S. patent application Ser. Nos. 11/238,240; 11/319,291;

11/327,880; 11/375,638; 11/393,991; and 11/396,309, all of which are incorporated by reference.

FIG. 1 illustrates schematically one embodiment of a stimulation system 100. The stimulation system includes a control module (e.g., a stimulator or pulse generator) 102, a paddle body 104, and at least one lead body 106 coupling the control module to the paddle body. The paddle body 104 and the lead body 106 form a lead. The paddle body 104 typically includes an array of electrodes 134. The control module 102 typically includes an electronic subassembly 110 and optional power source 120 disposed in a sealed housing 114. The control module 102 typically includes a port 144 (see FIG. 2) into which the proximal end of the lead body 106 can be plugged to make an electrical connection via contacts on the control module and lead body. It will be understood that the system for stimulation can include more, fewer, or different components and can have a variety of different configurations including those configurations disclosed in the stimulation system references cited herein. For example, instead of a paddle body, the electrodes can be disposed in an array at or near the distal end of the lead body 106 forming a percutaneous lead, as illustrated in FIG. 2. The percutaneous lead may be isodiametric along the length of the lead. In addition, one or more lead extensions (not shown) can be disposed between the lead and the control module to extend the distance between the control module and the paddle body.

The stimulation system or components of the stimulation system, including one or more of the lead body 106, the paddle body 104 and the control module 102, are typically implanted into the body. The stimulation system can be used for a variety of applications including, but not limited to, brain stimulation, neural stimulation, spinal cord stimulation, muscle stimulation, and the like.

The electrodes 134 can be made using any conductive material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or lead body 106 are typically disposed in a non-conductive, biocompatible material including, for example, silicone, polyurethane, polyetheretherketone (PEEK), epoxy, and the like or combinations thereof. The paddle body 104 and lead body 106 may be formed in the desired shape by any process including, for example, molding (including injection molding), casting, and the like. The non-conductive material typically extends from the distal end of the lead to the proximal end. The non-conductive, biocompatible material of the paddle body 104 and the lead body 106 may be the same or different. The paddle body 104 and lead body 106 may be a unitary structure or can be formed as two separate structures that are permanently or detachably coupled together.

Conductive contacts are typically disposed at the proximal end of the lead for connection to corresponding conductive contact in the control module 102 (or to conductive contacts on a lead extension). Conductive wires extend from the conductive contacts to the electrodes 134. Typically, one or more electrodes are electrically connected to a contact. In some embodiments, each contact is only connected to one electrode. The conductive wires may be embedded in the non-conductive material of the lead or can be disposed in one or more lumens extending along the lead. In some embodiments, there is an individual lumen for each conductive wire. In other embodiments, two or more conductive wires may extend through a lumen. There may also be one or more lumens that open at, or near, the distal end of the lead, for example, for infusion of drugs or medication into the side of implantation of the paddle body.

Figure 4:
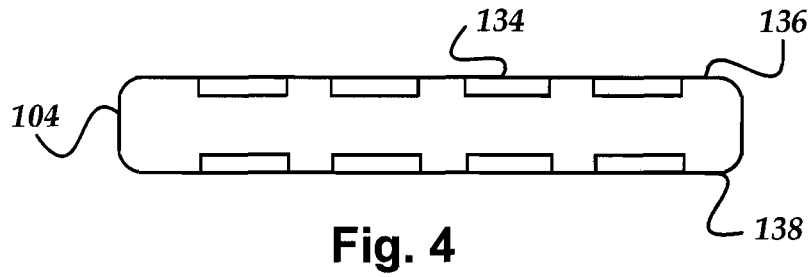
FIG. 4 is a schematic cross-sectional view of the paddle body of FIG. 3.

FIGS. 3 and 4 illustrate a schematic top view and a schematic cross-sectional view, respectively, of one embodiment of the paddle body 104 which includes an array of electrodes 134 disposed in a non-conductive material 132. A portion of the electrodes 134 are disposed on each of the opposing major surfaces 136, 138 of the paddle body. Each of these electrodes 134 is disposed entirely on one of the major surfaces 136, 138. An electrode is disposed "entirely" on a surface when the exposed portion of the electrode is found entirely on that surface. One advantage of this paddle lead arrangement over conventional paddle leads with electrodes on only one side of the paddle body is that the paddle lead of FIGS. 3 and 4 can be implanted without regard to which side of the lead is facing outside the body. This provides the professional implanting the lead with fewer concerns about proper positioning of the lead. Appropriate electrodes can be selected from either side of the paddle body 104 to stimulate the desired tissue region. For instance, the electrodes can stimulate either neural elements deeper than the paddle body, more superficial than the paddle body, or both. For example, in applications of peripheral nerve stimulation it may be desirable to stimulate a nerve trunk (perhaps to achieve broad paresthesia) located deep near the fascia, or it may be desirable (perhaps to achieve more localized stimulation) to stimulate smaller nerve branches and nerve endings located superficial to the paddle body.

In at least some embodiments, selection of the electrodes to provide electrical stimulation can be made by experimentation to determine which electrodes best stimulate the desired tissue. Various combinations of electrodes may be tested, for example, with the patient providing responses regarding the effects of stimulation of each particular combination of electrodes or the effect of the electrical stimulation can be observed instrumentally or visually.

The electrodes 134 in this embodiment and other embodiments described herein may be disposed in any arrangement on the major surface(s). For example, the electrodes 134 can be disposed in an array containing two or more columns or rows. The columns or rows can be aligned or staggered with respect to each other. Other arrangements can also be used including both irregular and regular arrangements (e.g., triangular, circular, or ellipsoidal arrangements.) The arrangements of electrodes 134 on the two major surfaces of the embodiment illustrated in FIGS. 3 and 4 can be the same, mirror images, or different.

The non-conductive material 132 of the paddle body 104 and lead body 106 can be made of any non-conductive, biocompatible material including, for example, silicone, polyurethane, polyetheretherketone (PEEK), epoxy, and the like or any combination thereof. The non-conductive material 132 may be formed in the desired shape by any process including, for example, molding (including injection molding), extruding, casting, and the like. Preferably, the non-conductive material does not cover the top surface (or at least a substantial portion of the top surface) of the electrodes 134.

Figure 5:
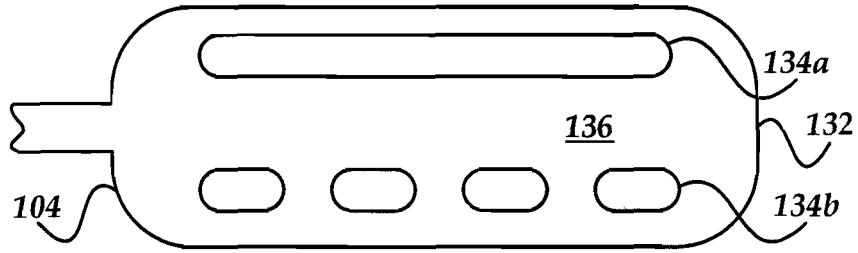
FIG. 5 is a schematic top view of another embodiment of a paddle body for use in an electrical stimulation system, according to the invention.

FIG. 5 illustrates a schematic top view of another embodiment of the paddle body 104 which includes at least one strip electrode 134a and an array of electrodes 134b disposed opposite the strip electrode 134a. As used herein, the term "strip electrode" is an electrode that has a length at least as long as two non-strip electrodes (e.g., electrodes 134b), and can be at least three times, four times, five times, or more longer than a non-strip electrode, and the strip electrode is disposed so that the strip electrode extends lengthwise at least opposite the center of two of the non-strip electrodes (and often extends lengthwise opposite the entirety of at least two, three, or four electrodes), as illustrated, for example, in each of FIGS. 5-7. The width of the strip electrode 134a and array electrodes 134b can be the same or different. In this embodiment, the strip electrode 134a can act as an anode with one or more of the array electrodes 134b acting as a cathode or vice versa. For example, this embodiment might be useful in cases where it is desirable to precisely localize one polarity (e.g., the cathode), but is not considered critical to precisely localize the other polarity.

Figure 6:
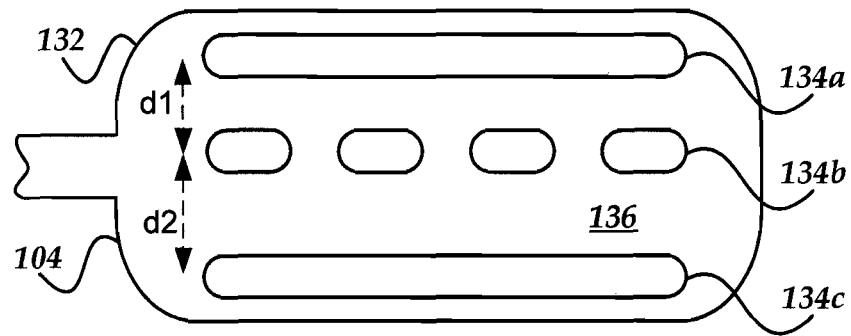
FIG. 6 is a schematic top view of a third embodiment of a paddle body for use in an electrical stimulation system, according to the invention.

FIG. 6 illustrates a schematic top view of yet another embodiment of the paddle body with two strip electrode 134a, 134c and an array of electrodes 134b disposed between the two strip electrodes. In at least some embodiments, the lateral distance d1 between strip electrode 134a and array electrodes 134b and the lateral distance d2 between strip electrode 134c and array electrodes 134b can be the same or, as illustrated in FIG. 6, different. This particular arrangement, where d1≠d2, can be used to provide a number of different electrode configurations for stimulation including tripolar (using electrodes 134a, 134b, and 134c), bipolar with electrode separation of d1 (using electrodes 134a, 134b), bipolar with electrode separation of d2 (using electrodes 134c, 134b), and bipolar with electrode separation of d1+d2 (using electrodes 134a, 134c). The separation distances d1 and d2 can be selected based on the application for which the stimulation system will be used, or in cases when the optimal bipolar distance is not known prior to implant so the ability to select the bipolar distance post-implant is desirable. For example, for at least some subcutaneous stimulation applications the separation distances, d1 and d2, can be in the range of 3 to 12 mm.

It will be understood that the arrangement of electrodes 134a, 134b, and 134c (in FIG. 6) in any of the embodiments illustrated in FIGS. 5 and 6 can be provided only on one side of the paddle body 104 or electrode arrangements can be provided with electrodes disposed on both opposing major surfaces of the paddle body (although each electrode is disposed entirely on one major surface or the other). Alternatively, different electrode arrangements can be provided on the opposing major surfaces including arrangements that differ in the presence, absence, or number of strip electrodes and the arrangement and placement of the strip electrodes (if present) and array electrodes.

Figure 7:
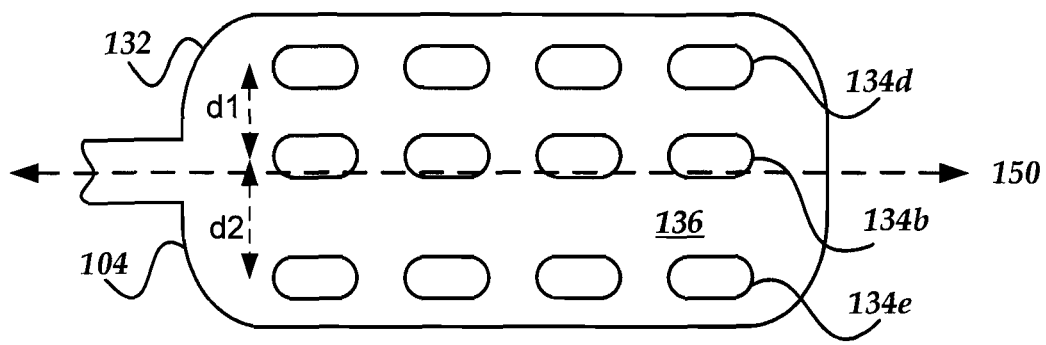
FIG. 7 is a schematic top view of a fourth embodiment of a paddle body for use in an electrical stimulation system, according to the invention.

FIG. 7 illustrates a schematic top view of yet another embodiment of a paddle body with three columnar arrays of electrodes 134b, 134d, and 134e where each array is arranged parallel to the longitudinal (i.e., long) axis 150 of the paddle body. The lateral distance d1 (the lateral distance is perpendicular to the longitudinal axis 150 of the paddle body) between array electrodes 134d and array electrodes 134b and the lateral distance d2 between array electrodes 134e and array electrodes 134b is different as illustrated in FIG. 7. It will be recognized that other embodiments may include additional columnar arrays of electrodes. Preferably, three adjacent columnar arrays are provided in the arrangement illustrated in FIG. 7 with different distances between each pair of adjacent columnar arrays.

This particular arrangement, where d1≠d2, can be used to provide a number of different electrode configurations for stimulation including tripolar (using electrodes 134b, 134d, and 134e), bipolar with electrode separation of d1 (using electrodes 134b, 134d), bipolar with electrode separation of d2 (using electrodes 134b, 134e), and bipolar with electrode separation of d1+d2 (using electrodes 134d, 134e). The separation distances d1 and d2 can be selected based on the application for which the stimulation system will be used, or in cases when the optimal bipolar distance is not known prior to implant so the ability to select the bipolar distance post-implant is desirable. For example, for at least some subcutaneous stimulation applications the separation distances, d1 and d2, can be in the range of 3 to 12 mm.

Figure 8:
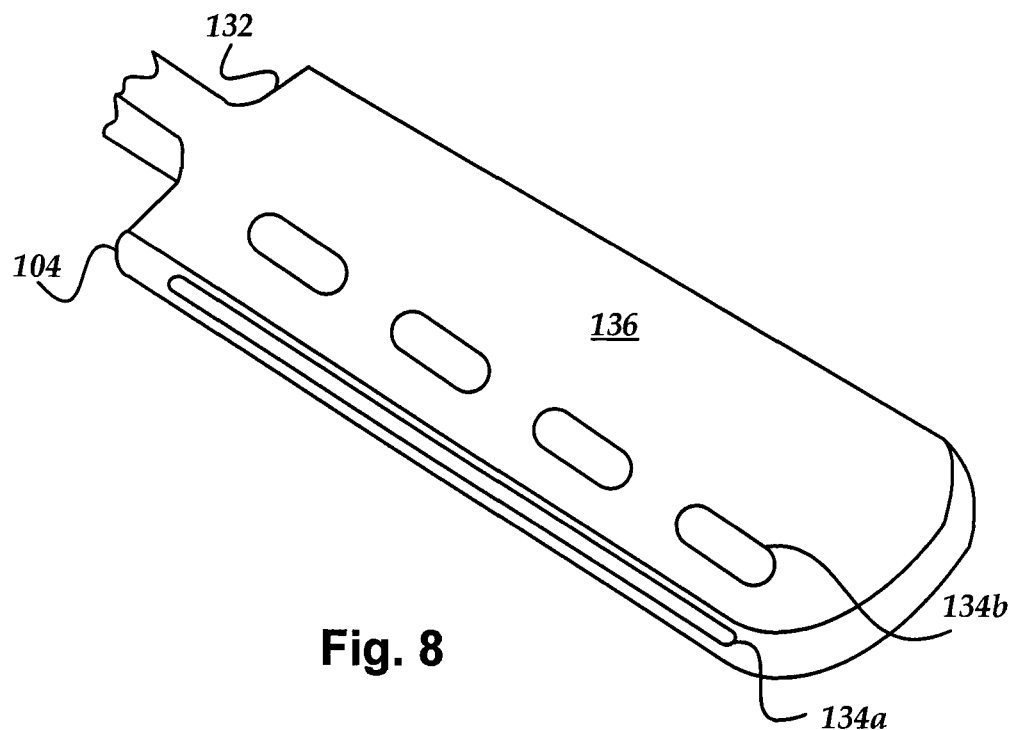
FIG. 8 is a schematic perspective view of a fifth embodiment of a paddle body for use in an electrical stimulation system, according to the invention.

FIG. 8 illustrates a schematic top view of another embodiment of the paddle body with a strip electrode 134a disposed entirely along a side surface 138 of the paddle body 104 and an array of electrodes 134b disposed entirely on a major surface 136. One potential advantage of this configuration is that the width of the major surface 136 of the paddle body may be made smaller, if desired, because only one array of electrodes is provided on the major surface particularly if that array only includes one column of electrodes. Multiple columns of electrodes could also be provided so that, for example, bipolar stimulation with variable electrode separation distance is available based on from which column the array electrode is selected. It will also be understood that an array of electrodes can be provided only on one major surface or arrays of electrodes can be provided on both opposing major surfaces of the paddle body. Likewise, a strip electrode may be provided on only one side surface or strip electrodes may be provided on both opposing side surfaces of the paddle body.

Figure 9:
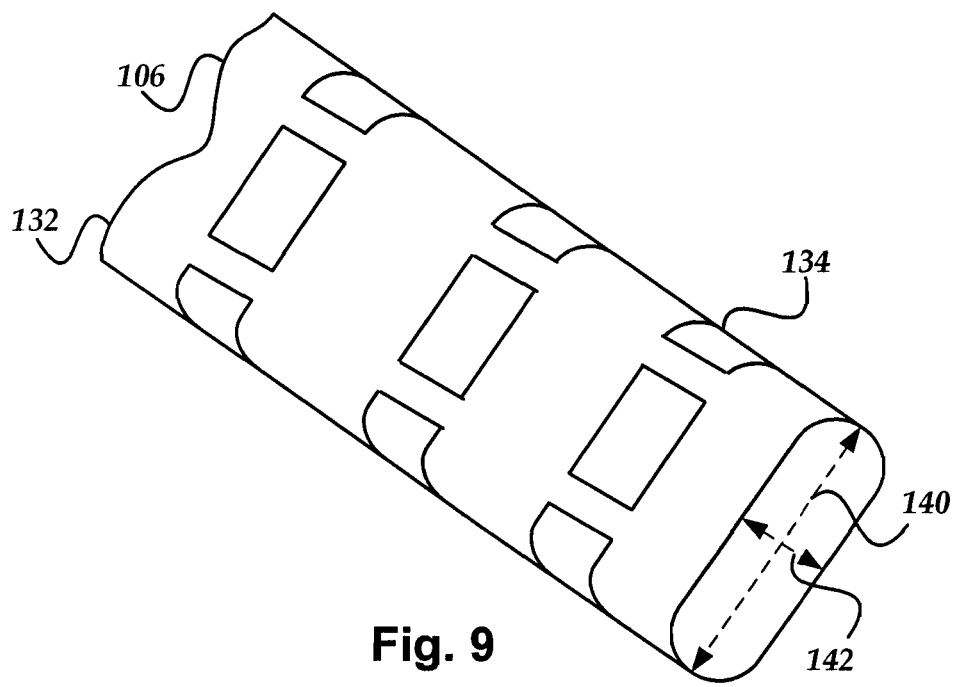
FIG. 9 is a schematic perspective view of one embodiment of a lead body with an ellipse-like cross-section for use in an electrical stimulation system, according to the invention.

FIG. 9 is a schematic perspective view of one embodiment of a lead body 106 with an ellipse-like cross-section and an array of electrodes 134. The ellipse-like cross-section has a major axis 140 and a minor axis 142 where the length of the major axis is greater than that of the minor axis. The ellipse-like cross-section may extend along substantially the entire length of the lead or only along a distal portion of the lead. Paddle bodies and leads with ellipse-like cross-sections are typically more flexible along the narrower or minor axis than along the broader or major axis. This directionality of the flexibility may be advantageous in at least some instances.

The array of electrodes 134 includes separate sets 142 of electrodes disposed along the length of the lead body 106 as well as separate electrodes 134 in each set disposed around the circumference of the lead. The spacing between sets of electrodes and between individual electrodes may be the same or different. In one embodiment, the array of electrodes 134 includes one or more sets 142 that have electrodes arranged uniformly around the circumference of the lead body 106, for example, at regular intervals (e.g., at 60°, 72°, 90°, or 120° intervals) around the circumference of the lead body 106.

Figure 10:
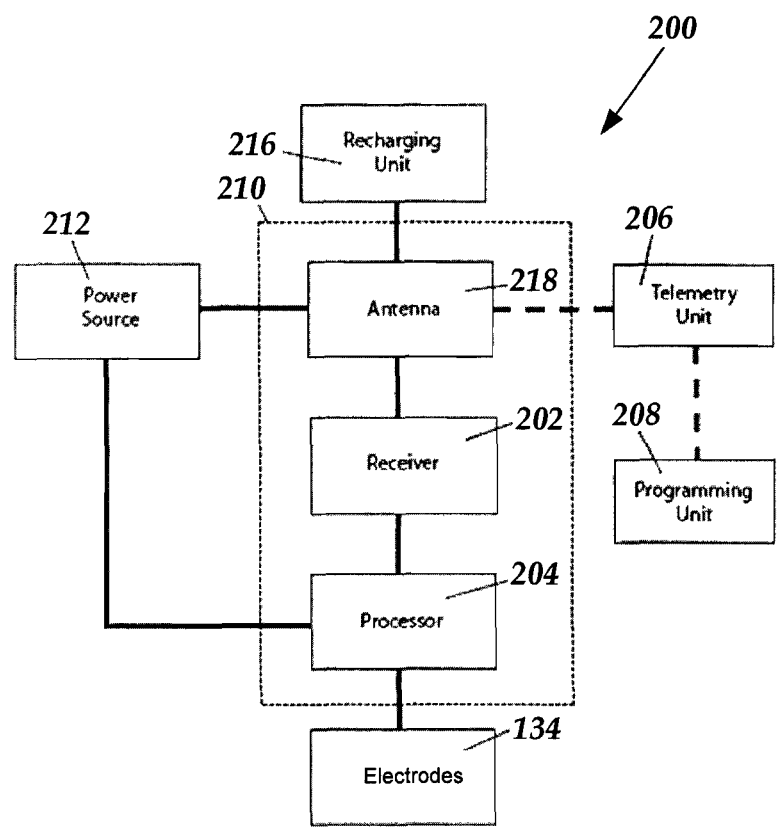
FIG. 10 is a schematic block diagram of components in one embodiment of an electrical stimulation system, according to the invention.

FIG. 10 is a schematic overview of one embodiment of components of a stimulation system 200 including an electronic subassembly 210 disposed within a control module. It will be understood that the stimulation system can include more, fewer, or different components and can have a variety of different configurations including those configurations disclosed in the stimulator references cited herein.

Some of the components (for example, power source 212, antenna 218, receiver 202, and processor 204) of the stimulation system can be positioned on one or more circuit boards or similar carriers within a housing of an implantable pulse generator, if desired. Any power source 212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 218 or a secondary antenna. The external power source can be in a device that is mounted on the skin of the user or in a unit that is provided near the user on a permanent or periodic basis.

If the power source 212 is a rechargeable battery, the battery may be recharged using the optional antenna 218, if desired. Power can be provided to the battery for recharging by inductively coupling the battery through the antenna to a recharging unit 216 external to the user. Examples of such arrangements can be found in the references identified above.

In one embodiment, electrical current is emitted by the electrodes 134 on the paddle or lead body to stimulate nerve fibers, muscle fibers, or other body tissues near the stimulation system. A processor 204 is generally included to control the timing and electrical characteristics of the stimulation system. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments, the processor may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 208 that, for example, allow modification of pulse characteristics. In the illustrated embodiment, the processor 204 is coupled to a receiver 202 which, in turn, is coupled to the optional antenna 218. This allows the processor to receive instructions from an external source to, for example, direct the pulse characteristics and the selection of electrodes, if desired.

In one embodiment, the antenna 218 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulation system. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 218 and receiver 202 can be used to modify or otherwise direct the operation of the stimulation system. For example, the signals may be used to modify the pulses of the stimulation system such as modifying one or more of pulse duration, pulse frequency, pulse waveform, and pulse strength. The signals may also direct the stimulation system to cease operation or to start operation or to start charging the battery. In other embodiments, the stimulation system does not include an antenna 218 or receiver 202 and the processor 204 operates as programmed.

Optionally, the stimulation system may include a transmitter (not shown) coupled to the processor and antenna for transmitting signals back to the telemetry unit 206 or another unit capable of receiving the signals. For example, the stimulation system may transmit signals indicating whether the stimulation system is operating properly or not or indicating when the battery needs to be charged. The processor may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed is:

1. A paddle lead, comprising:
a paddle body comprising a first major surface, a second major surface opposite the first major surface, and a first side surface connecting the first major surface to the second major surface;
a plurality of first electrodes disposed on the first major surface in at least one column, wherein at least four of the first electrodes are disposed in a first column; and
a first strip electrode disposed on the first side surface of the paddle body, wherein the first strip electrode opposes at least a center portion of the at least four first electrodes of the first column and is the only electrode disposed on the first side surface.

2. The paddle lead of claim 1, wherein the first strip electrode is straight.

3. The paddle lead of claim 2, wherein the paddle body further comprises a second side surface and the lead further comprises a second strip electrode disposed entirely on the second side surface.

4. The paddle lead of claim 3, wherein the first strip electrode is disposed on a portion of the first side surface that is opposite the portion of the second side surface on which the second strip electrode is disposed.

5. The paddle lead of claim 3, wherein the second side surface is opposite the first side surface.

6. The paddle lead of claim 2, further comprising a plurality of second electrodes disposed on a surface different from the first major surface.

7. The paddle lead of claim 6, wherein the plurality of second electrodes is disposed entirely on the second major surface.

8. The paddle lead of claim 7, wherein the first electrodes are disposed in at least two columns on the first major surface, each column containing a plurality of the first electrodes.

9. The paddle lead of claim 8, wherein the second electrodes are disposed in at least two columns on the second major surface, each column containing a plurality of the second electrodes.

10. The paddle lead of claim 1, further comprising a plurality of second electrodes disposed on the first major surface and disposed in a second column parallel to the first column.

11. The paddle lead of claim 1, wherein the first strip electrode opposes an entirety of at least four of the plurality of first electrodes which are arranged in a column parallel to the first strip electrode.

12. A stimulation system, comprising:
the paddle lead of claim 1; and
a control module coupleable to the paddle lead.

* * * * *